United States Patent
Lombardo et al.

(10) Patent No.: US 6,524,310 B1
(45) Date of Patent: Feb. 25, 2003

(54) SURGICAL CROSS-CONNECTING APPARATUS HAVING LOCKING LEVER

(75) Inventors: Alan Lombardo, Kinnelon, NJ (US); Michael Hammer, Pine Brook, NJ (US)

(73) Assignee: Blackstone Medical, Inc., Springfield, MA (US)

( * ) Notice: Subject to any disclaimer, the term of this patent is extended or adjusted under 35 U.S.C. 154(b) by 190 days.

(21) Appl. No.: 09/641,211

(22) Filed: Aug. 18, 2000

(51) Int. Cl.⁷ .............................................. A61B 17/70
(52) U.S. Cl. ........................................................ 606/61
(58) Field of Search ................................ 606/61, 69, 72

(56) References Cited

U.S. PATENT DOCUMENTS

| | | | |
|---|---|---|---|
| 4,085,744 A | | 4/1978 | Lewis et al. |
| 4,641,636 A | | 2/1987 | Cotrel |
| 4,815,453 A | | 3/1989 | Cotrel |
| 4,957,496 A | | 9/1990 | Schmidt |
| 5,002,542 A | * | 3/1991 | Frigg ........................ 606/61 |
| 5,005,562 A | | 4/1991 | Cotrel |
| 5,242,445 A | | 9/1993 | Ashman |
| 5,282,801 A | | 2/1994 | Sherman |
| 5,304,179 A | | 4/1994 | Wagner |
| 5,334,203 A | | 8/1994 | Wagner |
| 5,380,325 A | | 1/1995 | Lahille et al. |
| 5,437,669 A | | 8/1995 | Yuan et al. |
| 5,478,340 A | * | 12/1995 | Kluger ........................ 606/61 |
| 5,507,745 A | * | 4/1996 | Logroscino et al. .......... 606/61 |
| 5,507,747 A | | 4/1996 | Yuan et al. |
| 5,522,816 A | * | 6/1996 | Dinello et al. ................. 606/61 |
| 5,527,314 A | * | 6/1996 | Brumfield et al. ............. 606/61 |
| 5,531,747 A | | 7/1996 | Ray |
| 5,569,246 A | * | 10/1996 | Ojima et al. ................... 606/61 |
| 5,584,831 A | | 12/1996 | McKay |
| 5,643,264 A | | 7/1997 | Sherman et al. |
| 5,645,544 A | | 7/1997 | Tai et al. |
| 5,667,507 A | | 9/1997 | Corin et al. |
| 5,667,508 A | | 9/1997 | Errico et al. |
| 5,688,272 A | | 11/1997 | Montague et al. |
| 5,707,372 A | | 1/1998 | Errico et al. |
| 5,709,684 A | | 1/1998 | Errico et al. |
| 5,716,355 A | | 2/1998 | Jackson et al. |
| 5,743,911 A | * | 4/1998 | Cotrel ........................ 606/61 |
| 5,752,957 A | | 5/1998 | Ralph et al. |
| 5,810,818 A | | 9/1998 | Errico et al. |
| 5,947,966 A | | 9/1999 | Drewry et al. |
| 5,964,762 A | | 10/1999 | Biedermann et al. |
| 5,980,523 A | | 11/1999 | Jackson |
| 6,096,039 A | | 8/2000 | Stoltenberg et al. |
| 6,179,838 B1 | * | 1/2001 | Fiz ............................... 606/61 |
| 6,217,578 B1 | * | 4/2001 | Crozet et al. ................. 606/61 |
| 6,234,705 B1 | * | 5/2001 | Troxell ....................... 403/237 |
| 6,238,396 B1 | * | 5/2001 | Lombardo .................... 606/61 |
| 6,309,390 B1 | * | 10/2001 | Le Couedic et al. .......... 606/61 |
| 6,352,537 B1 | * | 3/2002 | Strnad ......................... 606/61 |

FOREIGN PATENT DOCUMENTS

| | | |
|---|---|---|
| EP | 611116 | 8/1994 |
| EP | 625337 | 11/1994 |
| FR | 2704137 | 10/1994 |
| SU | 1823791 | 6/1993 |

* cited by examiner

Primary Examiner—Todd E. Manahan
Assistant Examiner—David Comstock
(74) Attorney, Agent, or Firm—Dreier & Baritz, LLP

(57) ABSTRACT

Surgical cross-connecting apparatuses in which the components of the apparatuses are adjustable as a result of being provided with a number of degrees of freedom. The components are movable axially and rotatably. The components are rotatable in several different ways taken from the perspective of the axially extending cross connecting member of the apparatuses. The apparatuses include a lever and set screw for locking a spinal rod in position.

24 Claims, 5 Drawing Sheets

SURGICAL CROSS-CONNECTING APPARATUS HAVING LOCKING LEVER

BACKGROUND OF THE INVENTION

The present invention relates to a surgical cross-connecting apparatus and a cross-connecting surgical screw apparatus for use with implantation rods, and related methods of securing implantation rods using a surgical cross-connecting apparatus.

The bones and connective tissue of an adult human spinal column consists of more than 20 discrete bones coupled sequentially to one another by a tri-joint complex. The complex consists of an anterior disc and two posterior facet joints. The anterior discs of adjacent bones are cushioned by cartilage spacers referred to as intervertebral discs. The over 20 bones of the spinal column are anatomically categorized as one of four classification: cervical, thoracic, lumbar, or sacral. The cervical portion of the spine which comprises the top of the spine up to the base of the skull, includes the first 7 vertebrae. The intermediate 12 bones are thoracic vertebrae, and connect to the lower spine comprising the 5 lumbar vertebrae. The base of the spine is a sacral bones (including the coccyx).

The spinal column of bones is high complex in that it includes the over 20 bones coupled to one another, housing and protecting critical elements of the nervous system having innumerable peripheral nerves and circulatory bodies in close proximity. Despite its complexity, the spine is a highly flexible structure, capable of a high degree of curvature and twist in nearly every direction.

Genetic or developmental irregularities, trauma, chronic stress, tumors and disease, however, can result in spinal pathologies which either limit this range of motion, or which threatens the critical elements of the nervous system housed within the spinal column. A variety of systems have been disclosed in the art which achieve this immobilization by implanting artificial assemblies in or on the spinal column. These assemblies may be classified as anterior posterior or lateral implants. Lateral and anterior assemblies are coupled to the anterior portion of the spine which is in the sequence of vertebral bodies. Posterior implants generally comprise pairs of rods, which are aligned along the axis which the bones are to be disposed, and which are then attached to the spinal column by either hooks which couple to the lamina or attach to the transverse processes, or by screws which are inserted through the pedicles. In order to provide enhanced torsional rigidity, these implants generally include cross-connecting devices which couple the rods together transverse to the axis of the implants. These cross-connecting devices may couple directly to the rods themselves, or may be attached to the pedicle screws.

Exemplary prior art references include U.S. Pat. Nos. 5,005,562, 5,334,203, 5,688,272, 5,716,355, and 5,947,966.

It is desirable to provide cross-connecting devices that are adjustable and can form angular installments by taking advantage of various degrees of freedom possessed by components of the device.

SUMMARY OF THE INVENTION

The present invention is directed to surgical cross-connecting apparatuses in which the components of the apparatuses are adjustable as a result of being provided with a number of degrees of freedom. For instance, the components are movable axially and rotatably. The components are rotatable in several different ways taken from the perspective of the axially extending cross connecting member of the apparatuses.

In one embodiment, the surgical cross-connecting apparatus comprises a cross connecting member extending in an axial direction having at least one end provided with a hook that is mounted in an opening in the end, wherein the hook has an opening sized to receive a spinal rod, the hook being rotatable in the plane in which the cross connecting member extends, and a screw member fitted into an aperture which engages the spinal rod and locks the rod within the hook. In another embodiment, this hook is also provided at a second end of the cross connecting member.

In yet a further embodiment, the opening in the first end is a slot in which the hook is moveable in the axial direction in which the cross connecting member extends. In yet another embodiment, the cross connecting member is provided with a second end having a hook that is mounted in an opening in the second end, the opening of the second end being a slot in which the hook is moveable within the axial direction in which the cross connecting member extends.

Yet another embodiment is a surgical cross-connecting apparatus comprising at least one body positioned at an end of a cross connecting member extending in an axial direction, the body being provided with a cavity for receiving a spinal rod, a lever pivotally mounted to the body, a set screw mounted in a through hole in the lever that is positioned proximate to the cross connecting member so that the set screw bears against the cross connecting member when the set screw is tightened, wherein at least a portion of the lever defines a portion of the cavity. The body is rotatably mounted over the cross connecting member to rotate around the axial direction in which the cross connecting member extends. In yet another embodiment, in addition to having the body at a first end of the cross connecting member, a second end of the cross connecting member has an aperture, wherein the aperture is sized to receive an end of a hook, the end of the hook defining a second aperture in which means for fixing in place a spinal rod placed within the hook, wherein the hook is rotatable around the axis formed by the cross connecting member. In yet another embodiment, the bodies are located at both ends of the cross connecting member.

Still another embodiment is a surgical cross-connecting apparatus, comprising at least one body positioned at an end of a cross connecting member that extends in an axial direction, the end having a thickness that is less than the thickness of a central portion of the cross connecting member, the end being provided with a pin extending into a slot provided on the body, the body being provided with a cavity for receiving a spinal rod, a lever pivotally mounted to the body, a set screw mounted in a through hole in the lever that is positioned proximate to the cross connecting member so that the set screw bears against the cross connecting member when the set screw is tightened, wherein at least a portion of the lever defines a portion of the cavity. The pin is located on an underside of the cross connecting member and the slot is located on an underside of the body. The structure of this embodiment allows the body to rotate in the plane in which the cross connecting member extends. Also, the body is movable in the axial direction in which the cross connecting member extends. Other embodiments incorporate this body at a second end of the cross connecting member, or any of the other bodies previously described.

Yet another embodiment is a surgical cross-connecting apparatus comprising at least one body positioned at an end of a cross connecting member extending in an axial direction, the end having a thickness that is less than the thickness of a central portion of the cross connecting member, a first pin positioned adjacent the end of the cross connecting member, the pin inserted in an opening in the body, the body being provided with a cavity for receiving a spinal rod, a lever pivotally mounted to the body, a set screw mounted in a through hole in the lever that is positioned proximate to the cross connecting member so that the set screw bears against the cross connecting member when the set screw is tightened, wherein at least a portion of the lever defines a portion of the cavity. The body is rotatably mounted over the cross connecting member to rotate around the axial direction in which the cross connecting member extends. Other embodiments incorporate this body at a second end of the cross connecting member, or any of the other bodies previously described.

DETAILED DESCRIPTION OF THE PREFERRED EMBODIMENT

Figure 1:
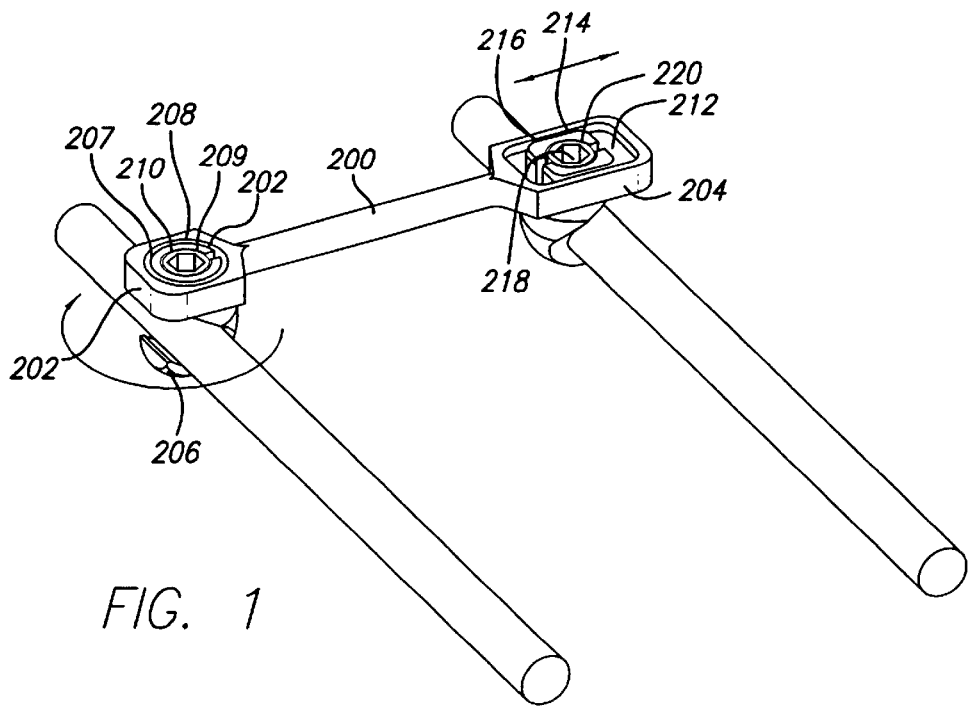
FIG. 1 is a perspective view of another embodiment of the surgical cross-connecting apparatus of the present invention.

FIG. 1 illustrates an embodiment of a cross-connecting apparatus. Here, cross connecting member 201 has a first end 202 and a second end 204. First end 202 is provided with a hook-shaped spinal rod engaging member 206 which is provided with an end 207 that is snap-fitted into aperture 208. A set screw 210 threaded through the aperture 209 in end 207 is engageable with the hook 206, which provides a means for clamping the spinal rods while simultaneously fixing the angular position of the hook. In other words, prior to being fixed in placed, the hook 206 is rotatable R in the plane in which the cross connecting member 201 extends. This permits the surgeon to more easily position the cross connecting on spinal rods which may be oriented obliquely to each other.

The second end 204 of the cross connecting member 201 is provided with a slotted opening 212 into which the end 216 of hook-shaped spinal rod engaging member 214 is snap fitted. The hook 214 can be moved in the axial direction in which the cross connecting member 201 extends by sliding the hook 214 in the slot. This provides a means for adjusting the axial distance between the spinal rods. The end 216 has an opening 218 in the middle thereof to receive a set screw 220 which engages threads provided on the opening of the end 216. As set screw 220 is tightened, it pushes against the spinal rod, locking it in place while simultaneously fixing the axial position of the hook.

Figure 2:
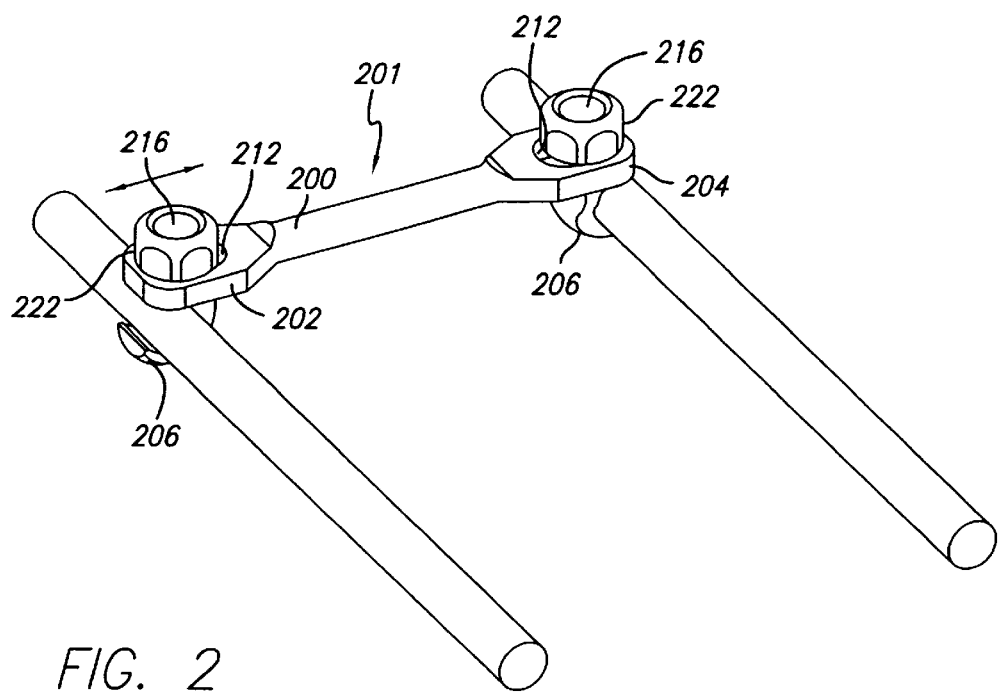
FIG. 2 is a perspective view of another embodiment of the surgical cross-connecting apparatus of the present invention.

In a further embodiment shown in FIG. 2, the cross connector is provided with slotted openings 212 at ends 202 and 204, which permit the hooks 206 to each move M within the axial direction A in which of the cross connecting member 201 extends. As shown in FIG. 2, threaded bolts 216, which extend from the hooks, pass through the slotted openings 212, and are held in the cross connecting member by locking nuts 222 which are threaded over the bolts. When the locking nuts 222 are tightened, the axial position of the hooks (i.e.—position along the axis formed by the cross connecting member 201) and angular position of the hook (i.e.—the angle at which a spinal rod intersects the cross connecting member 201 due to the position of the hook) are set. Prior to tightening the axial and angular position of the hooks are adjustable by the surgeon.

Figure 3:
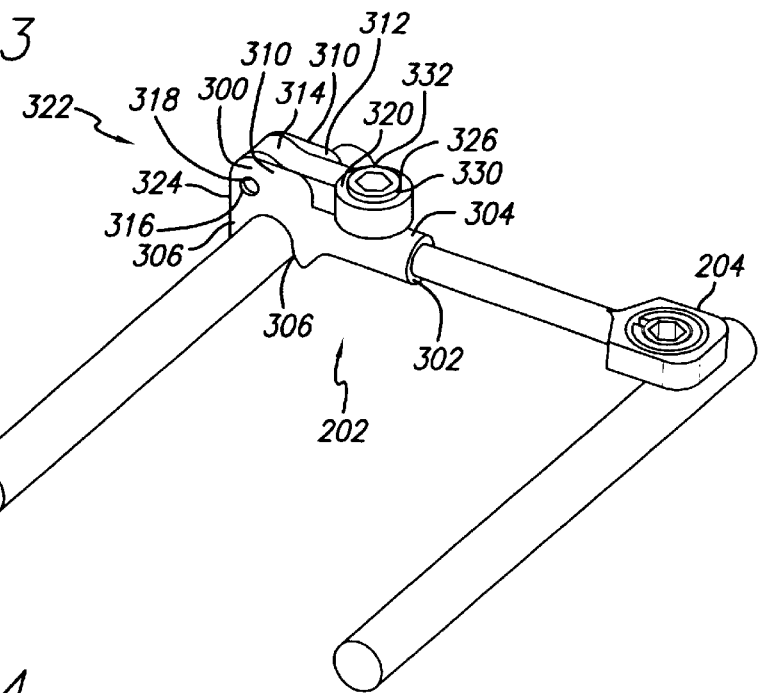
FIG. 3 is a perspective view of another embodiment of the surgical cross-connecting apparatus of the present invention.
Figure 4:
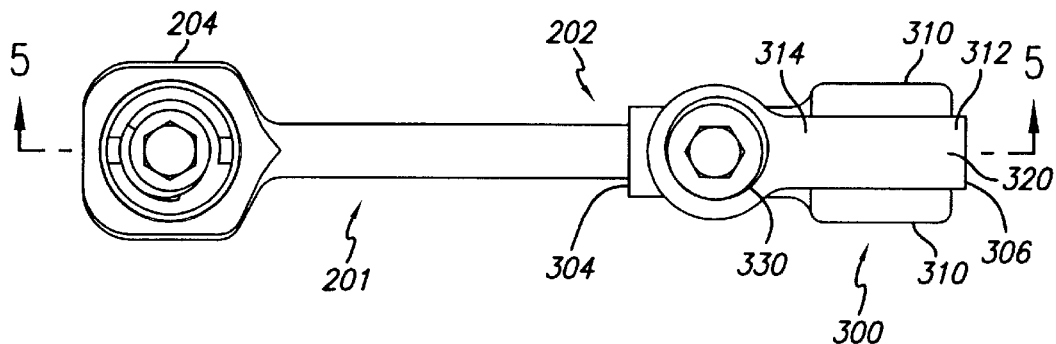
FIG. 4 is a top plan view of the FIG. 20 embodiment of the surgical cross-connecting apparatus of the present invention.
Figure 5:
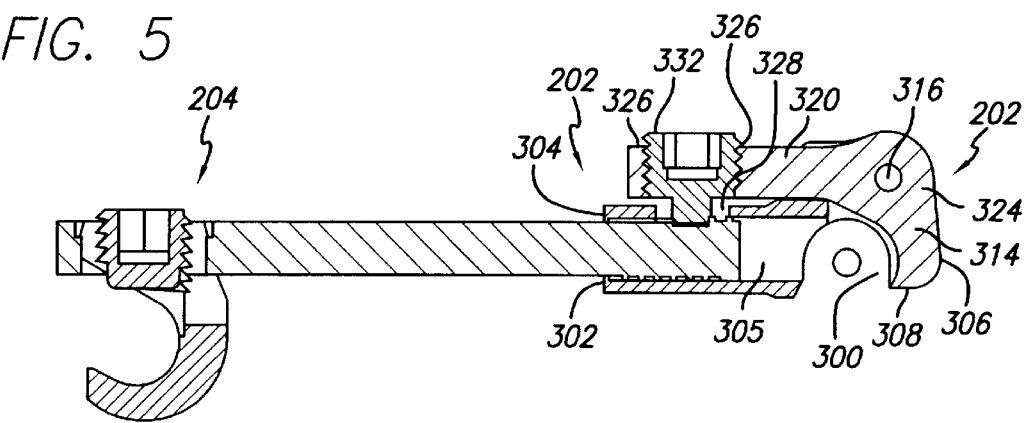
FIG. 5 is a view taken along line C—C of FIG. 21.

FIGS. 3, 4, and 5 show a further embodiment of the present invention. Cross connecting member 201 has first end 202 and second end 204. Though second end 204 as shown is the same as the one of the embodiment of FIG. 2, it can be any of the ends herein described, including the first end 202 that will now be described.

A body 300 is provided at the first end 202 of the cross connecting member 201. The body 300 has a first dimension which extends in the axial direction of the cross connecting member 201 and a second dimension which extends across the axial dimension of the cross connecting member 201. The body is constructed of a suitable durable material such as metal or plastic. The body is provided with an opening 302 at a first body end 304, which opens into a passageway 305 in the body extending in the axial direction. The opening 302 and passageway 305 are sized to receive the cross connecting member 201. Proximate the second body end 306, the body is provided with a cavity 308 that is sized to receive a spinal rod.

The body is provided with walls 310 on each side of the device which define a channel 312. The channel 312 extends in the axial direction from near the intermediate point of the device to the second end 306, and then in the cross axial direction along the second end 306. A lever 314 is mounted within the channel by a pin 316, which is fitted within a through hole 318 located in the walls 310 of the body that is placed within the second end.

The lever 314 is provided with two portions: a first lever portion 320 that extends in the axial direction of the cross connecting member 201, from the first body end 202 to the second body end 306, and an arm portion 324 which extends along the second body end in the cross axial direction. Together with the body 301, the arm portion 324 provides the walls of the cavity, so that arm portion 324 is located next to the spinal rod when it is placed in the cavity. The lever 314 is further provided with a through hole near the second end at the upper end of the body, which is sized and positioned to receive the pin, thereby mounting the lever 319 to the body.

Near the first body end 202, the first lever portion 320 is provided with a through hole 326 which is aligned with a through hole in the body 328. Each of these through holes extend in the cross axial direction. These through holes receive a set screw 330, which passes through the lever and through the body, and when tightened, forms a locking interference fit with the cross connecting member 201. As shown in FIG. 5, the set screw 330 is threaded on its exterior and it mates with a complimentary threaded profile provided on the through hole 326 on the first lever portion 320. The body 300 is rotatably mounted R over the cross connecting member 201 to rotate R around the axial direction in which the cross connecting member extends and is free to do so prior to tightening the set screw. This allows the surgeon to rotate the body around the cross connecting member 201, increasing the ease of positioning the cross connector on obliquely oriented rods.

The head 332 of the set screw 330 has a recess dimensioned and sized to receive a drill bit or screwdriver so that the set screw can be tightened or loosened to the locked or unlocked position. In FIGS. 20 and 21, the groove is shown as having a hexagonal shape, but other shapes are possible, such as a groove that can receive a flat head screwdriver.

When the set screw 330 is tightened, it moves through the through holes 326 and 328 and contacts the cross connecting member 201. Once contact is made, the screw can travel no further and it locks the cross connecting member into place. Further turning of the screw causes the lever to pivot, causing the arm portion 324 of the lever to contact the spinal rod, creating a tight fit between the lever and the spinal rod, locking the rod in the cavity. Since the lever can no longer pivot, the set screw is fixed in place against the cross connecting member, locking the cross connecting member in place.

Prior to tightening, the body is free to rotate around the axial direction in which the cross connecting member extends. This provides a degree of freedom that the surgeon is free to take advantage of and adjust the device to suit the specific needs of the patient. Once suitable adjustments are made, the device is tightened as aforedescribed.

Further embodiments, shown in FIGS. 6A–D, include further modifications on the embodiment of FIGS. 3–5. In these further embodiments, the body, lever, and set screw are generally the same as shown and described with respect to FIGS. 3–5, except as indicated below. The cross connecting member 201 is provided with a flat planar region 340 at the first end 202. The flat planar region 340 is provided on the top side 345 and the underside 346 of the cross connecting member. The flat planar region 340 has a reduced thickness relative to the central portion 342 of the cross connecting member 201. The flat planar region 340 is received in the body through the opening 302.

Figure 6A:
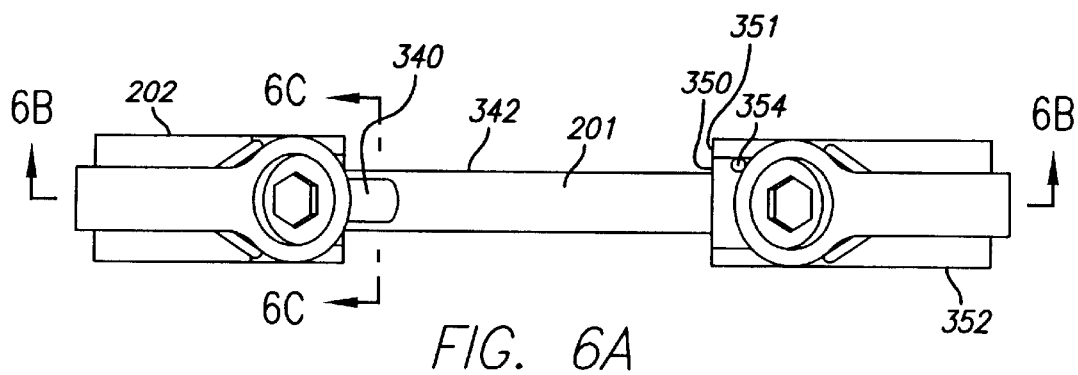
FIG. 6A is a top plan view of another embodiment of the surgical cross-connecting apparatus of the present invention.
Figure 6B:
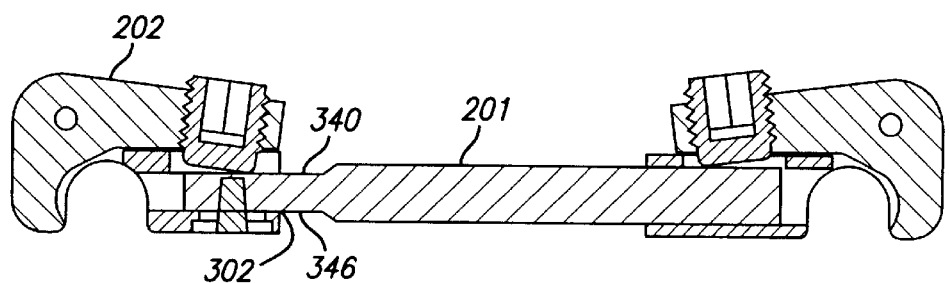
FIG. 6B is a view taken along line B—B of the embodiment of FIG. 6A.
Figure 6C:
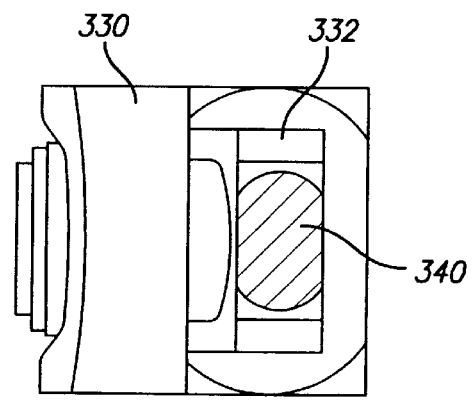
FIG. 6C is a view taken along line A—A of the embodiment of FIG. 6A.
Figure 6D:
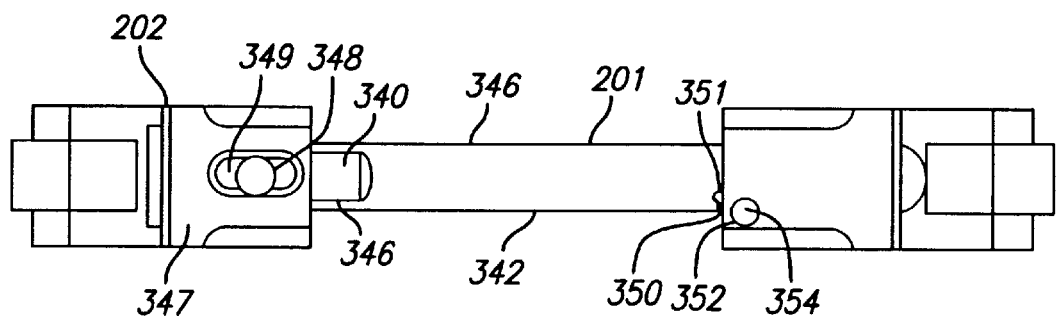
FIG. 6D is a bottom plan view of the embodiment of FIG. 6A.
Figure 7:
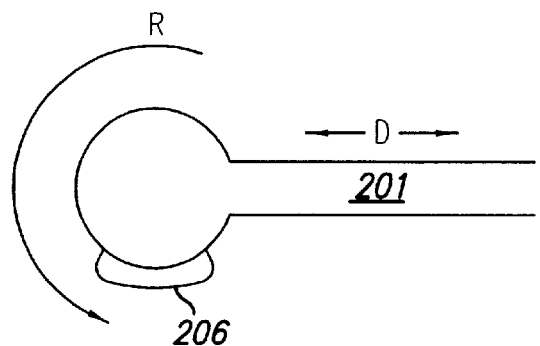
FIG. 7, a top plan view, illustrates "hook 206 rotatable R in the plane P in which the cross connecting member 201 extends."
Figure 8:
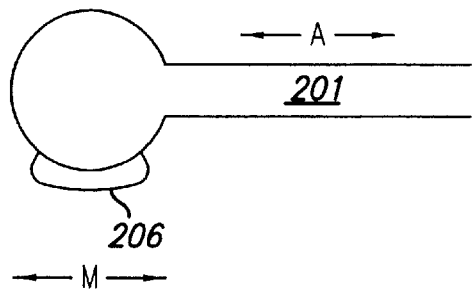
FIG. 8, a top plan view, illustrates "hook 206 [or body 300] is moveable M within the axial direction A in which the cross connecting member 201 extends."
Figure 9:
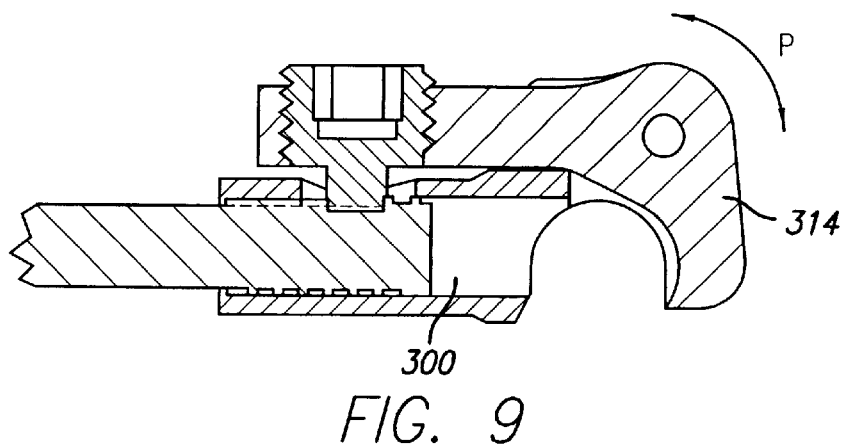
FIG. 9, a side elevational view, illustrates "lever 314 pivotally mounted P to the body 300."
Figure 10:
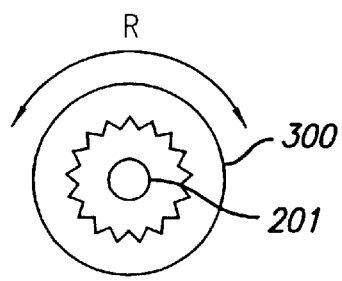
FIG. 10, an end elevational view illustrates "body 300 is rotatably mounted R over the cross connecting member 201 to rotate R around the axial direction in which the cross connecting member 201 extends."
Figure 11:
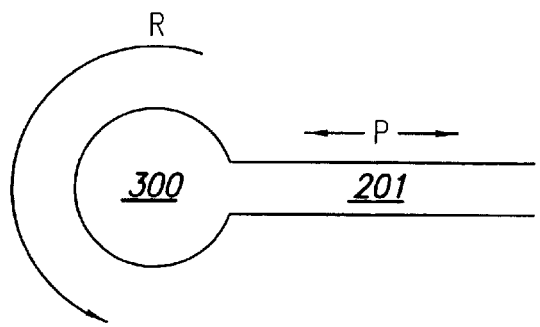
FIG. 11, a top plan view, illustrates "body 300 [can] rotate R in the plane P in which the cross connecting member 201 extends."

Referring to FIG. 6D, the underside 346 of the flat planar region 340 of the cross connecting member 201 is provided with a pin 348 which is received in a slot provided 349 on the underside 347 of the body. The cross connecting member 201 is rotatable in the plane P in which the cross connecting member 201 extends. Furthermore, the slot 349 may be sized to have a length dimension greater than the length dimension of the pin, wherein the length dimension extends in the axial direction of the cross connecting member 201.

Thus, the body 300 is moveable M within the axial direction in which the cross connecting member 201 extends, providing a further degree of movement that the surgeon can use to adjust the distance between the spinal rods prior to tightening the set screw. When the set screw bears upon the cross connecting member when it is tightened, fixing the body against the cross connecting member 201.

In a further embodiment, also shown in FIGS. 6A–D, the cross connecting member is provided at the second end with a flat planar region 350 which renders the end of cross connecting member received in the body less thicker on the lateral sides 351 of the cross connecting member. That is, the flat planar region 350 is less thick than the central portion 342 cross connecting member 201. The body is provided with a through hole 352 placed adjacent the flat planar region of the cross connecting member. A pin 354 is placed in the through hole 352. In this embodiment, the body rotatably mounted R over the cross connecting member 201 to rotate around the axial direction in which the cross connecting member 201 extends. However, rotation is limited to about 30° by the pin. This is due to the pin residing within space that would be occupied by the cross connecting member if the flat planar region did not exist in the cross connecting member. As the cross connecting member is rotated the edge of the flat planar region comes into contact with the pin, limiting the rotational movement of the cross connecting member.

The various components of the cross connector apparatus described and illustrated in the embodiments of the invention discussed above are preferably constructed of a titanium metal alloy. Numerous modifications and variations of the present invention are possible in light of the above teachings. It is therefore to be understood that within the scope of the attendant claims appended thereto, this invention may be practiced otherwise than as specifically disclosed herein.

What is claimed is:

1. A surgical cross-connecting apparatus, comprising:
at least one body positioned at an end of a cross connecting member extending in an axial direction, the body being provided with a cavity for receiving a spinal rod, a lever pivotally mounted to the body, a set screw mounted in a through hole in the lever that is positioned proximate to the cross connecting member so that the set screw bears against the cross connecting member when the set screw is tightened, wherein at least a portion of the lever defines a portion of the cavity.

2. The surgical cross-connecting apparatus of claim 1 wherein the body is rotatably mounted over the cross connecting member to rotate around the axial direction in which the cross connecting member extends.

3. The surgical cross-connecting apparatus of claim 1 wherein the lever mounted around a pin located at a second end of the body.

4. The surgical cross-connecting apparatus of claim 1 wherein the body has a through hole aligned with a through hole in the lever.

5. The surgical cross-connecting apparatus of claim 1 wherein the lever has a first portion extending in the axial direction in which the cross connecting member extends and an arm portion which extends across the axial direction in which the cross connecting member extends, wherein the arm portion is positioned within an opening in the body and moves against a spinal rod placed within the cavity when the lever pivots.

6. The surgical cross-connecting apparatus of claim 1 wherein the cross connecting member has a first end and a second end, the second end of the cross connecting member having an aperture, wherein the aperture is sized to receive an end of a hook, the end of the hook defining a second aperture in which means for fixing in place a spinal rod placed within the hook; wherein the hook is rotatable in the plane in which the cross connecting member extends.

7. The surgical cross-connecting apparatus of claim 1 wherein a body is positioned at a second end of the cross connecting member.

8. The surgical cross-connecting apparatus of claim 1 wherein the through hole in the lever is provided with threads that engage complimentary threads provided on the set screw.

9. A surgical cross-connecting apparatus, comprising:
at least one body positioned at an end of a cross connecting member that extends in an axial direction, the end having a thickness that is less than the thickness of a central portion of the cross connecting member, the end being provided with a pin extending into a slot provided on the body, the body being provided with a cavity for receiving a spinal rod, a lever pivotally mounted to the body, a set screw mounted in a through hole in the lever that is positioned proximate to the cross connecting member so that the set screw bears against the cross connecting member when the set screw is tightened, wherein at least a portion of the lever defines a portion of the cavity.

10. The surgical cross-connecting apparatus of claim 9 wherein the pin is located on an underside of the cross connecting member and the slot is located on an underside of the body.

11. The surgical cross-connecting apparatus of claim 9 wherein the body is rotatably mounted over the cross connecting member to rotate in the plane in which the cross connecting member extends, and the body is movable within the axial direction in which the cross connecting member extends.

12. The surgical cross-connecting apparatus of claim 9 wherein the lever mounted around a pin located at a second end of the body.

13. The surgical cross-connecting apparatus of claim 9 wherein the body has a through hole aligned with a through hole in the lever.

14. The surgical cross-connecting apparatus of claim 9 wherein the lever has a first portion extending in the axial direction in which the cross connecting member extends and an arm portion which extends across the axial direction in which the cross connecting member extends, wherein the arm portion is positioned within an opening in the body and moves against the spinal rod when the lever pivots.

15. The surgical cross-connecting apparatus of claim 9 a body is positioned at a second end of the cross connecting member.

16. The surgical cross-connecting apparatus of claim 9 wherein the through hole in the lever is provided with threads that engage complimentary threads provided on the set screw.

17. A surgical cross-connecting apparatus, comprising:
at least one body positioned at an end of a cross connecting member extending in an axial direction, the end having a thickness that is less than the thickness of a central portion of the cross connecting member, a first pin positioned adjacent the end of the cross connecting member, the pin inserted in an opening in the body, the body being provided with a cavity for receiving a spinal rod, a lever pivotally mounted to the body, a set screw mounted in a through hole in the lever that is positioned proximate to the cross connecting member so that the set screw bears against the cross connecting member when the set screw is tightened, wherein at least a portion of the lever defines a portion of the cavity.

18. The surgical cross-connecting apparatus of claim 17 wherein the body is rotatably mounted over the cross connecting member to rotate around the axial direction in which the cross connecting member extends.

19. The surgical cross-connecting apparatus of claim 17 wherein the lever is mounted on a pin located at a second end of the body.

20. The surgical cross-connecting apparatus of claim 17 wherein the body has a through hole aligned with a through hole in the lever.

21. The surgical cross-connecting apparatus of claim 17 wherein the lever has a first portion extending in the axial direction in which the cross connecting member extends and an arm portion which extends across the axial direction in which the cross connecting member extends, wherein the arm portion is positioned within an opening in the body and moves against the spinal rod when the lever pivots.

22. The surgical cross-connecting apparatus of claim 17 wherein two bodies are mounted on the cross connecting member.

23. The surgical cross-connecting apparatus of claim 22 wherein the through hole in the lever is provided with threads that engage complimentary threads provided on the set screw.

24. The surgical cross-connecting apparatus of claim 17 wherein the body is positioned at a first end of the cross connecting member, and a second body is mounted over a second end of the cross connecting member, the second end having a thickness that is less than the thickness of a central portion of the cross connecting member, the second end being provided with a second pin extending into a slot provided on the body, the second body being provided with a cavity for receiving a spinal rod, a lever pivotally mounted to the second body, a set screw mounted in a through hole in the lever that is positioned proximate to the cross connecting member so that the set screw bears against the cross connecting member when the set screw is tightened, wherein at least a portion of the lever is positioned adjacent the cavity.

* * * * *